US007326088B2

(12) United States Patent
Tulkki

(10) Patent No.: US 7,326,088 B2
(45) Date of Patent: Feb. 5, 2008

(54) REDUCING LEAKAGE CURRENT IN GUIDE WIRE ASSEMBLY

(75) Inventor: Sauli Tulkki, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 527 days.

(21) Appl. No.: 10/983,904

(22) Filed: Nov. 9, 2004

(65) Prior Publication Data

US 2006/0099834 A1 May 11, 2006

(51) Int. Cl.
*A61N 1/375* (2006.01)
*H01R 24/04* (2006.01)

(52) U.S. Cl. ........................................ 439/669; 607/37

(58) Field of Classification Search ................ 439/668, 439/669; 607/37; 600/585
See application file for complete search history.

(56) References Cited

U.S. PATENT DOCUMENTS 4,119,103 A 10/1978 Jirak
6,196,980 B1 3/2001 Akerfeldt et al.
6,428,336 B1 8/2002 Akerfeldt
6,663,570 B2 12/2003 Mott et al.
6,741,892 B1 * 5/2004 Meadows et al. ........... 607/116
2004/0098068 A1 5/2004 Carbunaru et al.
2004/0180581 A1 9/2004 Von Malmborg et al.
2005/0043770 A1 * 2/2005 Hine et al. .................... 607/37

* cited by examiner

*Primary Examiner*—Neil Abrams
(74) *Attorney, Agent, or Firm*—Foley & Lardner LLP

(57) ABSTRACT

The present invention relates to a method and a device for reducing leakage current in a guide wire assembly having conductor members (707, 708) arranged at a connector end of the guide wire (702) to provide electrical contact with electrical leads (705, 706) of the guide wire and to provide signals transferred via the electrical leads to an external device, said conductor members being separated by at least one insulator (709). An idea of the present invention is to minimize leakage current via the at least one insulator. When a physician places the guide wire into an appropriate location in the body, a male connector (100) of the guide wire may be contaminated by, for example, dirt, fat, moisture, etc., which is attached to the physician's fingers and deposited onto the male connector. An electrode (710) mounted at the female connector is used to apply a guard potential (Ud) to the insulator (709) to reduce potential difference and thereby reduce current leakage between members (707, 708).

30 Claims, 10 Drawing Sheets

REDUCING LEAKAGE CURRENT IN GUIDE WIRE ASSEMBLY

TECHNICAL FIELD OF THE INVENTION

The present invention relates to a method and a device for reducing leakage current in a guide wire assembly having conductor members arranged at a connector end of the guide wire to provide electrical contact with electrical leads of the guide wire and to provide signals transferred via the electrical leads to an external device, said conductor members being separated by at least one insulator.

BACKGROUND ART

Guide wires are generally known in the art. Their use is, for example, in connection with treatment of coronary disease. As is conventional, a contrast media is used in connection with an x-ray of a blood vessel to show occlusion, however, without showing a cross section of a stenosis. Complicating the diagnosis of the problem is that different patients have different blood flow. Measurement of blood pressure is a way to diagnose the significance of the stenosis. In practice, a distal end of the guide wire is inserted into the body, for example into an opening into the femoral artery, and placed at a desired location. At the distal end of the guide wire is a miniature sensor arranged for measuring pressure. Further, once the guide wire is placed by the physician into the appropriate location, a catheter of appropriate type may be guided onto the guide wire. A balloon dilation may then be performed.

Electrical leads extending along the guide wire carry measurement signals from the sensor via connectors to a monitor for further processing. The guide wire is electrically connected through a male connector arranged at a proximal end of the guide wire, via a female connector, to the monitor. At the male connector, there are one conductor member arranged for each lead extending along, or inside, the guide wire. Insulating spacers are arranged to separate the conductor members. On insertion of the male connector in the female connector, the conductor members are brought into electric contact with corresponding female contact members.

When the physician places the guide wire into the appropriate location in the body, the male connector may be contaminated by, for example, dirt, fat, moist, etc., which is attached to the physician's fingers and deposited onto the male connector. Alternatively, body fluids such as blood may be deposited onto the connector when the guide wire is inserted in the body. In another scenario, to permit replacement or exchange of the catheter, the male connector is disconnected from the female connector and the catheter is removed over the guide wire. At that time, body fluids will be deposited directly onto the male connector and indirectly onto the female connector, via the male connector. Hence, the connectors may be contaminated by blood and other bodily fluids at the time the catheter is changed, and these body fluids will potentially alter the electrical properties of the connector. As a further consequence, the contaminations given above may deteriorate the insulation between the conductor members in the connectors, and measured values may become unreliable due to leakage currents flowing through the insulating spacers. Further, insulation may be deteriorated for other reasons, for example because of manufacturing defects.

A guide wire assembly with connectors is shown, for example, in U.S. Pat. No. 6,663,570, Mott et al. In U.S. Pat. No. 6,663,570, a system is disclosed for connecting a flexible elongate member arranged with an electrically operable sensor to a physiology monitor. The system comprises a flexible cable having an electrical conductor therein and a connector arranged on an end of the flexible cable for receiving an end of the flexible elongate member. A contact member in the connector is electrically connected to the conductor in the flexible cable to transfer data to the physiology monitor.

In this type of prior art guide wire assembly, bodily fluids and other contaminations can clearly cause electrical problems in the connector. Consequently, there remains a need for a connector which can be used with the restricted small size of a guide wire typically having a diameter of 0.35 mm, and which can be used in situations where there might be contamination by human or animal body fluid or contaminations such as dirt, fat or moist.

SUMMARY OF THE INVENTION

An object of the present invention is to solve the above given problems, and to provide a device in which leakage currents in the guide wire assembly is reduced, which leakage currents are due to bodily fluids or other contamination that deteriorates insulation capacity in the guide wire assembly. Leakage currents may also be due to general deteriorations in insulating capacity, for example arising from manufacturing defects.

A further object is to provide a more reliable guide wire assembly.

These objects are attained by a method of reducing leakage current in a guide wire assembly having conductor members arranged at a connector end of the guide wire to provide electrical contact with electrical leads of the guide wire and to provide signals transferred via the electrical leads to an external device, said conductor members being separated by at least one insulator, in accordance with claim 1.

These objects are also attained by a device for reducing leakage current in a guide wire assembly having conductor members arranged at a connector end of the guide wire to provide electrical contact with electrical leads of the guide wire and to provide signals transferred via the electrical leads to an external device, said conductor members being separated by at least one insulator, in accordance with claim 13.

According to a first aspect of the present invention, there is provided a method comprising the steps of applying a guard potential to said at least one insulator, which guard potential is arranged to reduce a potential difference across the insulator such that leakage current is reduced.

According to a second aspect of the present invention, there is provided a device comprising an electrode arranged to apply a guard potential to said at least one insulator, which guard potential is arranged to reduce a potential difference across the insulator such that leakage current is reduced.

An idea of the present invention is to minimize leakage current via at least one insulator arranged to separate conductor members in a guide wire assembly. As previously described, when a physician places the guide wire into an appropriate location in the body, the male connector of the guide wire may be contaminated by, for example, dirt, fat, moist, etc., which is attached to the physician's fingers and deposited onto the male connector. Alternatively, body fluids such as blood may be deposited onto the male connector when the guide wire is inserted in the body. When connecting the male and female connector, the contaminations are attached to the insulator of the male connector, and the insulating capacity of the insulator is hence deteriorated, i.e. insulating resistances between conductor members are decreased. As a consequence, leakage current will flow via the insulator and a potential difference is created across the insulator. Clearly, the electrical properties of the connectors will be altered. As a direct consequence, measured physiological values will become unreliable. Therefore, at the insulator, a guard voltage is applied. This guard potential is arranged to reduce the potential difference across the insulator. When this potential difference is reduced, ideally to zero voltage, the leakage current is reduced correspondingly. Note that fluids not necessarily must be deposited onto the insulator for the present invention to be advantageously implemented in a guide wire assembly. Deterioration in insulating capacity of the insulator may be remedied by means of the present invention, even though the deterioration has emerged under other circumstances.

In a guide wire assembly comprising a miniature sensor for measuring physiological variables, leads extending along, or inside, the guide wire carry measurement signals from the sensor via connectors to an external device, such as a monitor, for display and/or further processing. In the following example, it is assumed that a first lead carries a pressure signal and a second lead is set to a reference potential, typically ground. Note that the lead being coupled to a reference voltage, such as ground, is not regarded as a signal lead, as no actual measurement signal is transferred via that particular lead. In case two leads are utilized, there are typically two corresponding conductor members arranged at the connector end of the guide wire for coupling the sensor signal carried by one of the leads to the external monitor, and for connecting the other lead to a common ground. An insulating guide wire sheath extends along the guide wire and ends at a first conductor member, which couples the pressure signal out of the guide wire assembly. Adjacent to the first conductor member is the insulator separating the first conductor member from a second conductor member, which is connected to ground, or some other appropriate reference potential. As previously described, bodily fluids will deteriorate the insulating capacity of the insulator, but by applying the guard potential to the insulator by means of an electrode, the potential difference across the insulator, with respect to the adjacently located conductor member to which the signal carrying lead is connected, is reduced and the corresponding leakage current will be reduced accordingly. This is highly advantageous, as the problem relating to unreliable sensor values due to leakage currents in the connector is eliminated.

According to further embodiments of the present invention, which are advantageous when the guide wire sheath is conductive, an additional guard potential is applied. When the guide wire sheath is conductive, an additional insulator must be used. This additional insulator is located adjacent to the guide wire sheath, i.e. between the guide wire sheath and a conductor member. The insulating capacity of the additional insulator may, for reasons previously described, also deteriorate when bodily fluids, dirt, fat, moist, etc. are disposed on the connector. More general problems causing deterioration, for example manufacturing defects, may also be overcome by the present invention. To reduce a potential difference across the insulator arranged adjacent to the guide wire sheath, such that leakage current is reduced, the additional guard potential is applied to the additional insulator or the guide wire sheath by means of an additional electrode. The application of the guard potential to the guide wire sheath has the further advantage that a potential reducing effect can be utilized at a distal part of the guide wire, towards the sensor. Suppose a deterioration in insulating capacity occurs between an electrical lead and the guide wire sheath; a leakage of current will then occur between the lead and the guide wire sheath. This current will be reduced in the same manner as at the insulator(s) arranged at the guide wire proximal end, by applying the guard potential to the guide wire sheath.

Preferably, the previously described guard potential and the additional guard potential of the present embodiment are set to be the same potential, derived from the same drive element. Said electrode and said additional electrode will hence be driven from the same potential.

According to another embodiment of the invention, a sensor electrode is arranged at a conductor member located adjacent to an insulator across which a potential difference is to be reduced. The voltage of the signal at the conductor member can hence be measured and supplied as guard potential. By measuring the signal voltage level at the conductor member of interest, the voltage level of the guard potential can be set to be identical to the signal voltage level, which has as a result that the potential difference across the insulator(s) can be reduced to a minimum. By means of sensing the signal voltage level and providing a guard potential based on that level via the electrodes arranged to supply the guard potential, a closed loop control system for controlling leakage current is provided.

According to another embodiment of the present invention, which advantageously can be employed in case two or more signals are transferred via respective signal leads and the guide wire has a conductive sheath as previously described, an averaged signal is employed as guard potential via the guard potential electrodes.

In the following, it is assumed that a first lead carries a pressure signal, a second lead carries a temperature signal and a third lead is set to a reference potential, typically ground. In case of three leads, there are typically three corresponding conductor members arranged at the connector end of the guide wire for coupling the sensor signals carried by two of the leads to the external monitor, and for connecting the third lead to a common ground. A conductive guide wire sheath extends along the guide wire and ends at a first insulator, which insulates the sheath from the first conductor member located on the other side of the first insulator, along the guide wire axis. The first insulator couples the pressure signal out of the guide wire assembly. Adjacent to the first conductor member is a second insulator separating the first conductor member from the second conductor member, which couples the temperature signal out of the guide wire assembly. A third insulator insulates the second conductor member from the third, grounded conductor member. In this particular embodiment, two sensor signals (plus a common ground) are transferred along the guide wire, but it should be noted that any other number of sensor signals may be transferred, and the principle of this embodiment may be applied to said any number of sensor signals.

The potentials at the first and second conductor members generally have the same voltage level, which has the effect that no leakage current will flow through the second insulator separating the first and second leads, since no potential difference is present across the second insulator. However, due to bodily fluids there will be a potential difference across the first insulator located between the first conductor member and the guide wire sheath, as well as across the third insulator located between the second conductor member and the third, grounded conductor member. As a consequence, there will be leakage currents via the first and the third insulators, respectively.

By sensing a voltage level of a signal at a conductor member located adjacent to a respective insulator across which a potential difference is to be reduced, i.e. at the first and the second conductor members, by means of a sensing electrode, creating an averaged signal having as a voltage level an average value of the two sensed voltage levels, and supplying said averaged signal as guard potential via a guard potential electrode to the third insulator and either (a) the first insulator or (b) the guide wire sheath, the potential difference across the first and the third insulators is reduced and the corresponding leakage current will be reduced accordingly.

According to yet a further embodiment of the present invention, as an alternative to measuring a voltage level of a signal at a conductor member by means of a sensor electrode, the voltage level in question may be estimated, and the estimated voltage level may be supplied as guard potential for reducing leakage current. Possibly, the voltage level at the contact member is known empirically or by know-how regarding the sensor. In that case, there is no need to measure the signal, and hardware associated with the measurement may be omitted. By means of estimating the signal voltage level and providing a guard potential based on that level via the guard potential electrode(s), an open loop control system for controlling leakage current is provided.

When using the approach of estimating the signal voltage level instead of actually measuring the signal level, it is still possible to use an averaged signal as guard potential, as described above. If two or more signals are transferred via respective signal leads and the guide wire has a conductive sheath, and the estimating approach is employed, the averaged signal is calculated by taking the average value of the estimates of the signal voltage levels at the respective conductor member. Subsequently, the averaged signal is supplied as guard potential.

In still another embodiment of the present invention, the sensed voltage level is low pass filtered, such that a DC voltage level is provided as guard potential. This is advantageous in case the sensor signal, i.e. the signal representing a measured physiological variable, is used to modulate a carrier signal, the modulated signal being received at a corresponding conductor member.

According to still a further embodiment of the present invention, a voltage regulating circuit is arranged for setting and supplying the guard potential to (i) a first insulator across which a potential difference is to be reduced, (ii) a first and a second insulator across which a potential difference is to be reduced, or (iii) a first insulator across which a potential difference is to be reduced and the guide wire sheath arranged adjacent to a second insulator across which a potential difference is to be reduced. Preferably, the voltage regulating circuit for supplying the guard potential acts as a buffer and hence has a (very) high input impedance and a (very) low output impedance. Hence, the sensed signal voltage levels may be connected to the insulators or the sheath via this voltage regulating circuit, creating a closed loop control system. In an embodiment of the invention, the voltage regulating circuit for supplying the guard potential comprises an operational amplifier configuration, such as a voltage follower. In another embodiment of the present invention, the voltage regulating circuit for setting the guard potential comprises a microprocessor having an A/D-converter and a D/A-converter as an interface to the surrounding environment. In case a microprocessor is employed, the previously mentioned averaged signal can be created in the microprocessor by calculating an average value of the concerned signal voltage levels.

In yet another embodiment of the present invention, a sample and hold circuit is arranged at the input of the operational amplifier configuration for repeatedly sampling the voltage level supplied to the operational amplifier. In this embodiment, the guard potential is updated repeatedly by sampling the sensed signal at a particular instance of time and holding the value of the sampled signal by charging a capacitor until the next sample is taken. Sample and hold functionality may alternatively be implemented in the microprocessor. In an alternative embodiment, the guard potential is updated once, after insertion of the male connector into the female connector, by sampling the sensed signal at one instance of time and holding the value of the sampled signal by charging a capacitor.

Typically, the device for reducing leakage current in the guide wire assembly according to the present invention is arranged at a female connector for the guide wire assembly, such that the guard potential is applied to the insulator(s) when the male connector arranged at the connector end of the guide wire is inserted into the female connector to provide signals transferred via the signal leads to an external device.

Further features of, and advantages with, the present invention will become apparent when studying the appended claims and the following description. Those skilled in the art realize that different features of the present invention can be combined to create embodiments other than those described in the following.

BRIEF DESCRIPTION OF THE DRAWINGS

Preferred embodiments of the present invention will be described in detail in the following with reference made to accompanying drawings, in which.

DETAILED DESCRIPTION OF PREFERRED EMBODIMENTS OF THE PRESENT INVENTION

Figure 1:
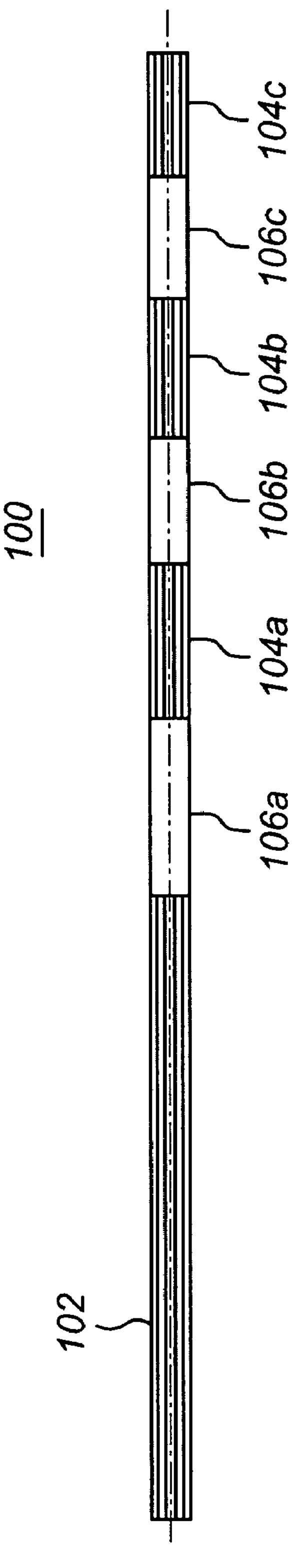
FIG. 1 shows an exemplifying male connector comprised in a guide wire assembly.

In FIG. 1, a male connector 100 is depicted. It is located at the proximal end of a guide wire 102, the guide wire and the connector having essentially the same diameter. The male connector 100 is comprised of three conductive cylindrically shaped members 104*a, b* and *c,* one for each lead required in the guide wire 102, separated by means of insulating spacers 106*a, b* and *c,* referred to as insulators. The insulators are preferably made of a molded polymer material. The insulating material can be, for example, a two-component epoxy adhesive. The insulators 106*a, b* and *c* perform the function in the assembled male connector of spacing apart the core wire from the conductor members 104*a, b* and *c*. Thus, the conductor members are electrically insulated from the core wire. They also space the conductor members apart from each other and the sheath of the guide wire, in case the sheath is conductive. On insertion of the male connector in a female connector (shown in FIG. 2), each of the conductive cylindrically shaped members 104*a, b* and *c* is brought into contact with a corresponding female contact member. A guide wire having a suitable male connector is disclosed in, for example, the applicant's U.S. Pat. No. 6,196,980.

A distal end of the guide wire (not shown) is inserted into a body, for example into an opening into a femoral artery, and advanced to a desired location. At the distal end of the guide wire is a miniature sensor arranged for measuring physiological parameters such as pressure and temperature. Electrical leads extending inside, or along, the guide wire carry measurement signals from the sensor via the guide wire to the conductor members 104*a, b* and *c*. The conductor members are made from any material of high conductivity. Preferably, they are machined of platinum. Other possible materials include stainless steel, gold and copper, etc. The guide wire typically comprises a core wire (not shown), which extends through the guide wire, forming the guide wire center. The core wire is conventionally used to prevent kinks, to provide strength to the guide wire, and to hold the guide wire together. Traditionally, it is made of a high strength material, such as, for example, stainless steel. Other high strength materials (including non-metallic materials) can be used. The core wire therefore should be as large a diameter as possible, while leaving room for the leads and other elements to fit within the catheter within which the guide wire will be used.

Figure 2:
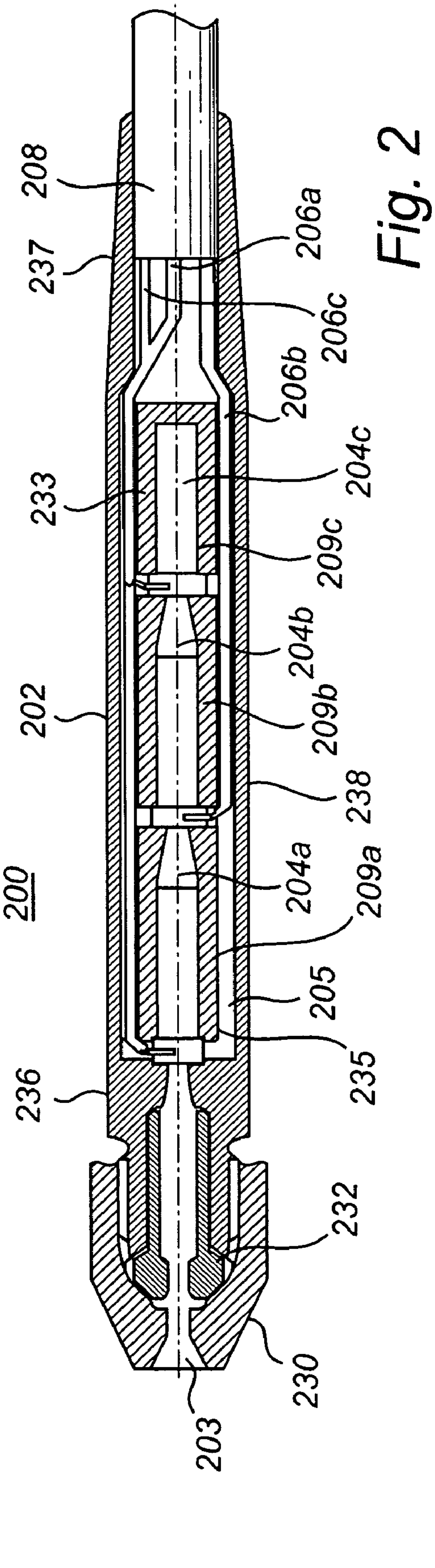
FIG. 2 shows an exemplifying female connector, which connector is illustrated in partial cross section, for a guide wire assembly.

FIG. 2 shows a female connector 200 illustrated in partial cross section. It has a distal end and a proximal end, the former adapted to receive the male connector via an opening 203. The female connector comprises an insulating hollow housing 202 having a distal portion 236, a proximal portion 237, and an intermediate portion 238 containing three hollow contact seats 209*a-c*, each contact seat being adapted to hold one of the contact members 204, the details of which will be described below. At the distal end of the female connector, a holding arrangement 230 and 232 for securing the male connector in said female connector are provided. In the proximal portion of the insulating housing 202, an opening in provided which is adapted to receive an interface cable 208, having a number of conductors 206. A suitable female connector is disclosed in, for example, the applicant's U.S. Pat. No. 6,428,336.

Figure 3:
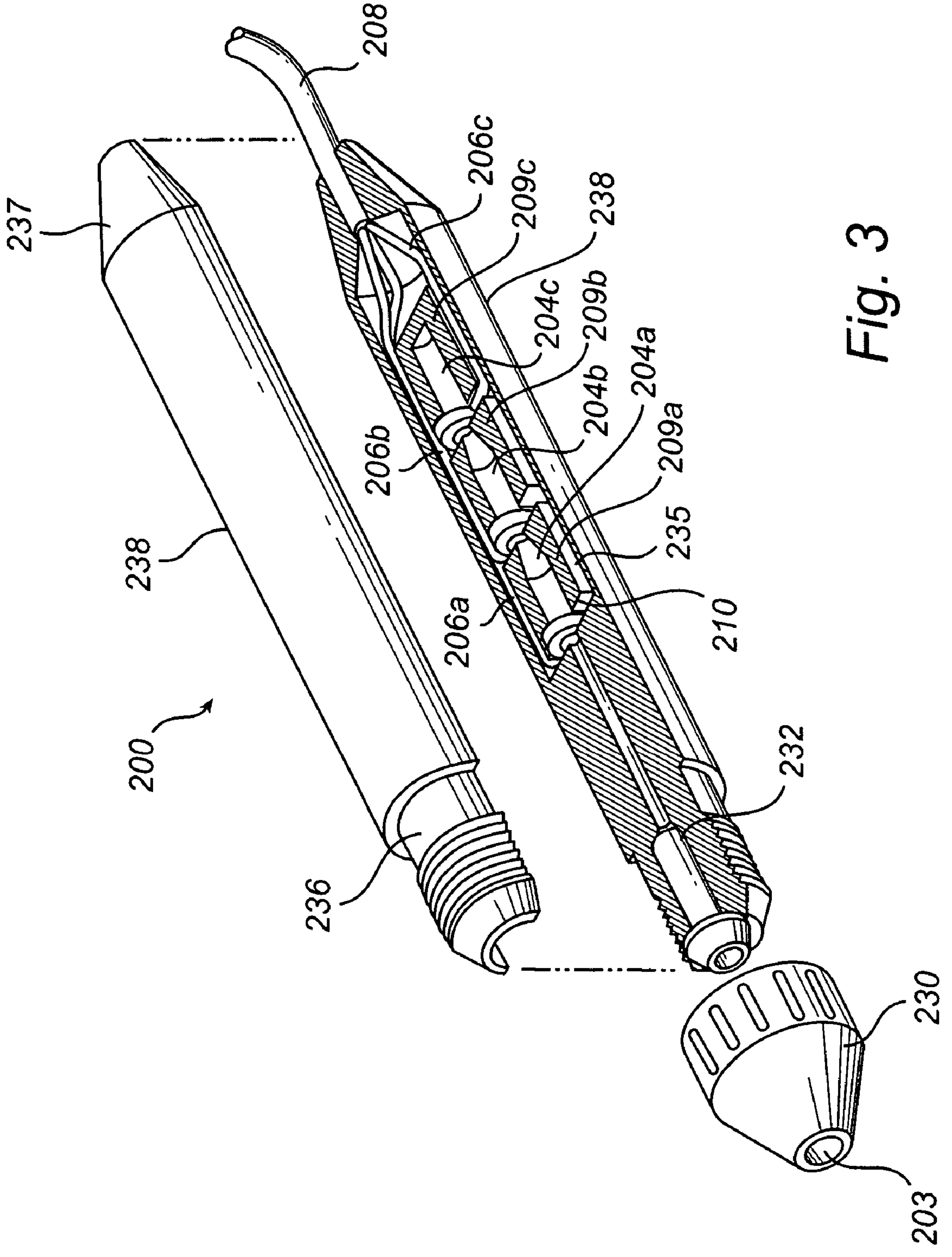
FIG. 3 shows a detailed illustration of the interior of the female connector of FIG. 2.

With reference to FIG. 3, which more clearly illustrates the interior of the female connector 200, the design of the contact structure of the connector will be described. Thus, in an intermediate portion 238 of the connector, contact seats 209*a-c*, extending axially along the portion are provided, separated from each other. Each contact seat is formed between two walls and adapted to hold one of the contact members 204, and is thus formed with a recess 210 having a shape and dimensions exactly corresponding to the shape and dimensions of a contact member 204, i.e. the recess in each seat is hemi-cylindrical. The most proximal contact seat is confined by a single U-shaped wall 233 (see FIG. 2). A wall 235 of the insulating housing and the walls of the contact seats in the contact portion define a space 205 where the conductors 206 from the interface cable can be located so as to reach each contact member. The three hollow contact members 204 are disposed one in each of the contact seats in the insulating housing at a distance axially from each other. Preferably, the contact member 204*c* located at the proximal end has a closed bottom. The number of contact members (in this case three) is chosen according to the required number of conductors, 206*a, b* and *c*, in the interface cable 208 and/or the number of conductors for transferring signals from the sensor along the guide wire. The conductors 206 from the interface cable 208, entering said housing at the proximal portion 237, are provided in said space between the wall 235 of the housing and the walls 233 and 235 as desired. Said conductors have a length sufficient to reach the respective contact members 204.

While the guide wire assembly has been described with reference to a male and a female connector having three contact members, it is to be understood that the number thereof is not critical. Also, said number must not necessarily be the same as the number of conductors in the interface cable, and can thus be higher or lower as appropriate.

Figure 4:
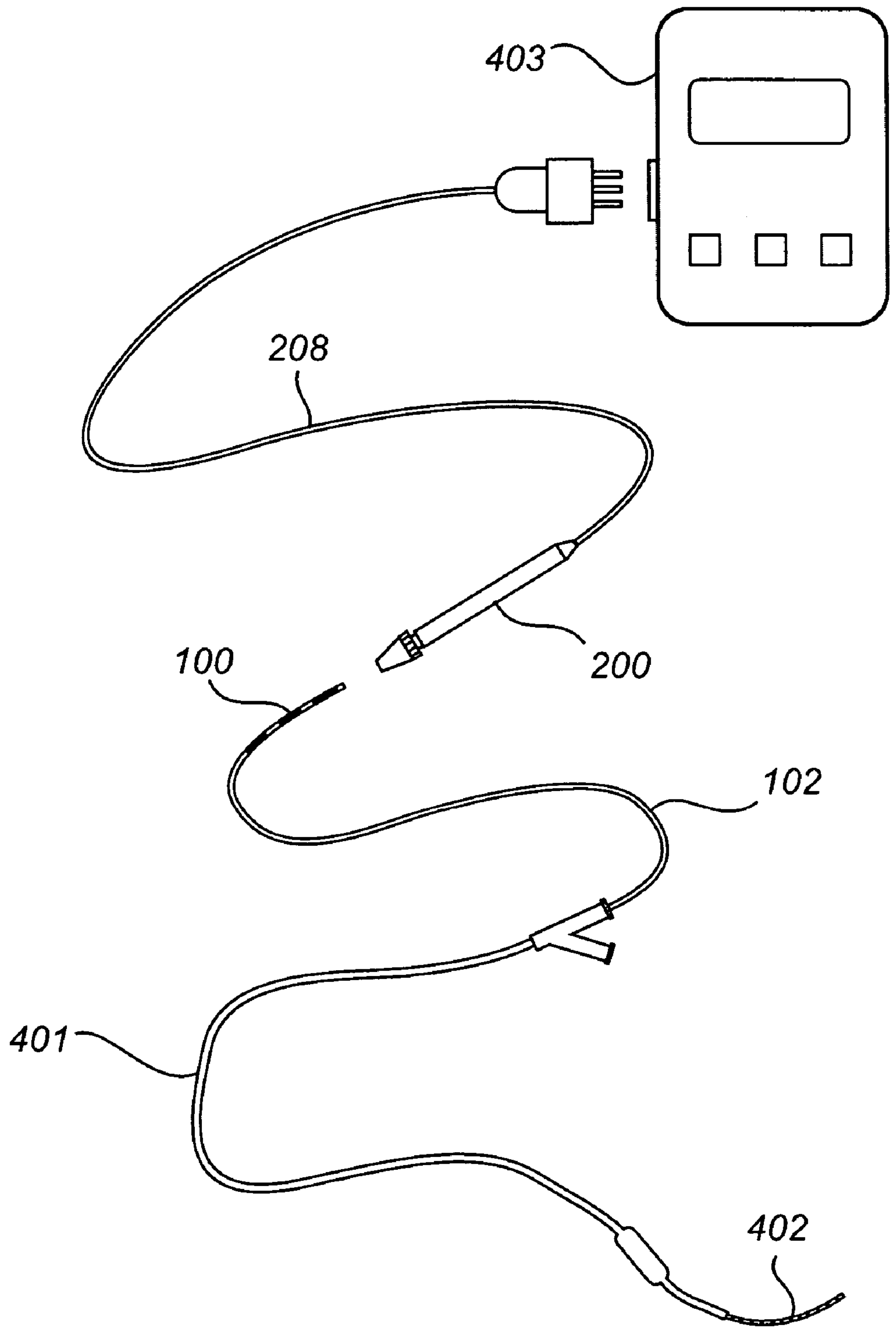
FIG. 4 shows an exemplifying guide wire assembly comprising a sensor, a guide wire, a male connector, a female connector and an interface cable.

FIG. 4 illustrates the male connector 100 on a guide wire 102. The guide wire 102 is inserted within a balloon catheter 401. At the distal end of the guide wire 102 is a sensor 402. The male connector 100 is inserted into a female connector 200. The female connector 200 is electrically connectable into a monitor device 403 via an interface cable 208. For definition purposes, a guide wire assembly comprises at least a sensor 402, a guide wire 102 and a male connector 100. In use, the guide wire assembly is connected to a female connector 200 and hence an interface cable 208. In practice, the distal end of the guide wire is inserted into the body, for example, into an opening into the femoral artery. Once placed by the physician into the appropriate location, a catheter 401 of the desired type is guided onto the guide wire 102. The guide wire is connected through the male connector 100 and the female connector 200 to a monitor 403. To permit replacement or exchange of the catheter 401, the male connector 100 is disconnected from the female connector 200, and the catheter is removed over the guide wire. At that time, body fluids would be deposited onto the connector.

Figure 5:
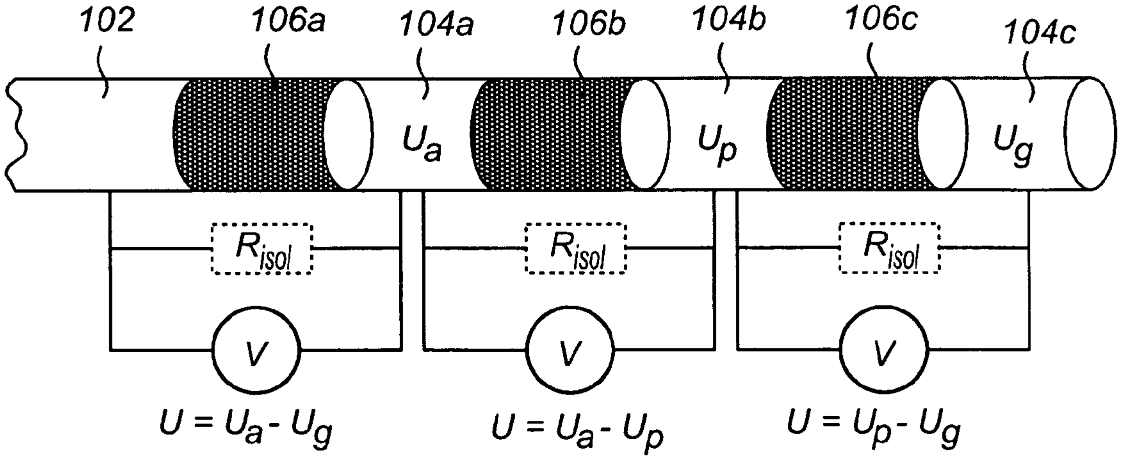
FIG. 5 shows a view of a male connector, which view illustrates insulating capacity of the insulators.

FIG. 5 illustrates a problem involved in prior art connectors, when body fluids or other insulation deteriorating contaminations are deposited onto them, or when insulation capacity is deteriorated for other reasons. If the sheath of the guide wire 102 is conductive, the potential difference across insulator 106*a* will be Ua–Ug, when the insulating capacity of the insulator is reduced. Note that the insulator 106*a* is omitted in case the guide wire sheath is composed of an insulating material. The potential difference across insulator

106*c* will be Up−Ug, which typically is the same as the potential difference across the insulator 106*a*. As a consequence, the voltage drop across insulator 106*b* is close to zero. The leakage current through the respective conductor members will be the potential difference across the conductor member divided by the insulating resistances of the insulators. The insulating resistance of the insulators will hence vary with the degree of damping of the insulators.

Figure 6:
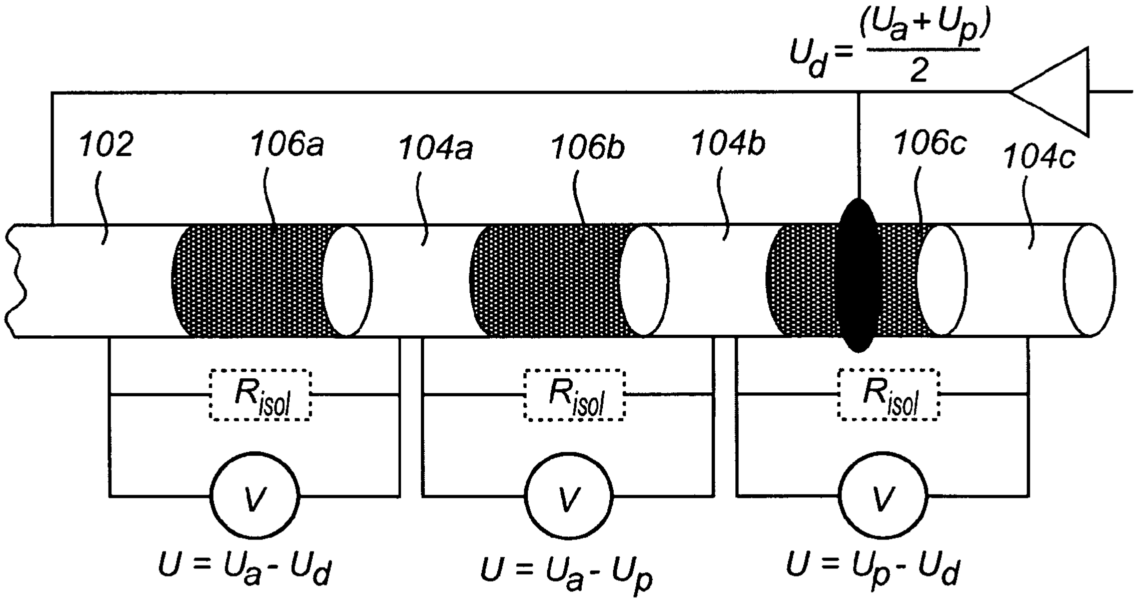
FIG. 6 shows a view of a male connector, which view illustrates how a leakage current problem may be overcome.

FIG. 6 shows an embodiment of the present invention to illustrate a basic idea of the invention, wherein a guard potential Ud is applied to reduce the voltage drop across insulators. The guard potential may for example be applied via an operational amplifier or a microprocessor. By applying the guard potential Ud to the sheath of the guide wire 102 and the insulator 106*c*, which guard potential preferably is equal to, or close to, the voltage at the conductor members 104*a* and 104*b*, the potential difference across the insulators 106*a* and 106*c* respectively will be reduced. Thus, the potential difference, Ua−Ud, across insulator 106*a* will be equal to the potential difference, Up−Ud, across insulator 106*c*, i.e. virtually zero. The leakage current is defined as the potential difference of the insulator divided by the insulating resistance of the insulator. Since the potential difference is zero, or close to zero, the leakage current is negligible. Note that the guard potential not necessarily is the average value of Ua and Up, but may be set to be equal to, for example Ua or Up, since the respective voltage levels at conductor members 104*a* and 104*b* are approximately the same.

In practice, the device for applying the guard potential is arranged at the female connector for the guide wire assembly. As a consequence, the guard potential is applied to an insulator when the male connector of the guide wire is inserted into the female connector to provide signals, which are transferred via the signal leads, to an external device.

Figure 7:
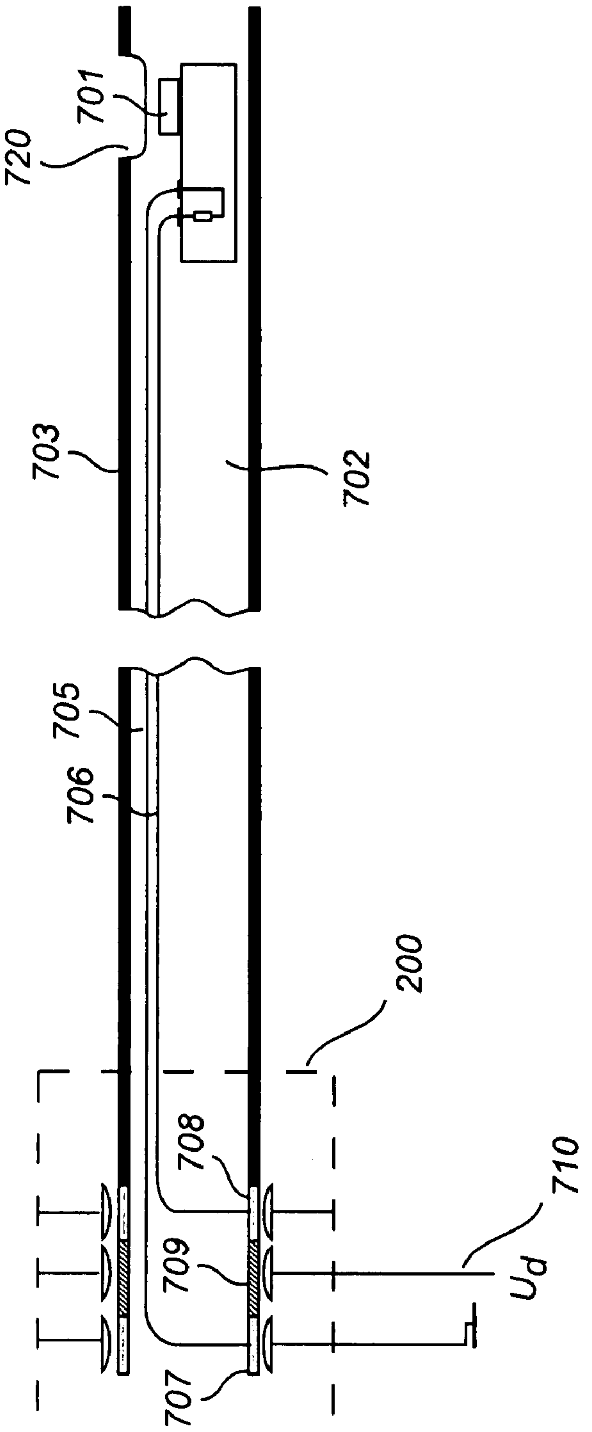
FIG. 7 shows an embodiment of the present invention, in which one signal carrying lead and an insulating guide wire sheath is employed.

FIG. 7 shows an embodiment of the present invention employing one signal carrying lead and an insulating guide wire sheath. A sensor 701 is mounted in a recess 720 of a guide wire 702. From the sensor 701, leads 705, 706 are arranged to carry measurement signals from the sensor via connectors to a monitoring device (not shown). In this particular example, it is assumed that a first lead 706 carries a pressure signal and a second lead 705 is coupled to ground when in an operative state, i.e. when inserted into a female connector. At the male connector end of the guide wire, there are two corresponding conductor members 707, 708 for coupling the sensor signal carried by the first lead 706 to the monitoring device, and for connecting the second lead 705 to ground. Note that the conductor members 707, 708 are coupled to the monitoring device and ground, respectively, on insertion of the male connector in a female connector (illustrated in FIG. 2), wherein each of the conductive cylindrically shaped members 707, 708 is brought into contact with a corresponding female contact member. An insulating guide wire sheath 703 extends along the guide wire 702 and ends at the first conductor member 708, which couples the pressure signal out of the guide wire assembly. Adjacent to the first conductor member is an insulator 709 separating the first conductor member 708 from the second conductor member 707. Consequently, when the male connector is inserted in the female connector, the insulator 709 will separate the two corresponding female contact members from each other. Application of a guard potential Ud to the insulator 709 by means of an electrode 710 will reduce a potential difference across the insulator with respect to the adjacently located conductor member 708 to which the signal carrying lead is connected. Hence, the corresponding leakage current will be reduced accordingly.

Figure 8:
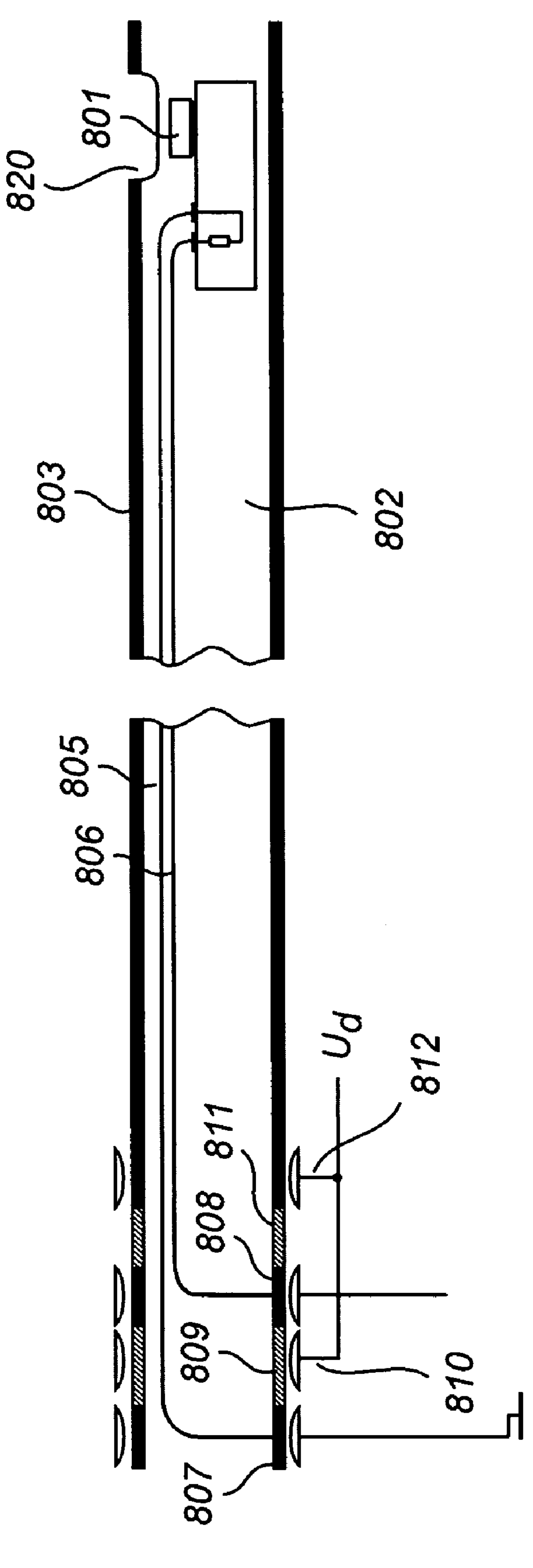
FIG. 8 shows another embodiment of the present invention, in which one signal carrying lead and a conductive guide wire sheath is employed.

FIG. 8 shows another embodiment of the present invention employing one signal carrying lead and a conductive guide wire sheath. A sensor 801 is mounted in a recess 820 of a guide wire 802, and leads 805, 806 are arranged to carry measurement signals from the sensor via connectors to a monitoring device (not shown). A first lead 806 carries a pressure signal and a second lead 805 is coupled to ground when in an operative state, i.e. when inserted into a female connector. At the male connector end of the guide wire, there are two corresponding conductor members 807, 808 for coupling the sensor signal carried by the first lead 806 to the monitoring device, and for connecting the second lead 805 to ground. Note that the conductor members 807, 808 are coupled to the monitoring device and ground, respectively, on insertion of the male connector in a female connector (illustrated in FIG. 2), wherein each of the conductive cylindrically shaped members 807, 808 is brought into contact with a corresponding female contact member. In this embodiment, a conductive guide wire sheath 803 extends along the guide wire 802 and ends at a second insulator 811. Adjacent to the first conductor member is a first insulator 809 separating the first conductor member 808 from the second conductor member 807. Application of a guard potential Ud to the first insulator 809 by means of an electrode 810 will reduce a potential difference across the first insulator 809 with respect to the conductor member 808 to which the signal carrying lead is connected. Hence, the corresponding leakage current will be reduced accordingly. Further, application of an additional guard potential, typically being the guard potential Ud applied to the first insulator 809, to the guide wire sheath 803 by means of the additional electrode 812 will reduce a potential difference across the second insulator 811 with respect to the conductor member 808. Hence, the corresponding leakage current will be reduced accordingly.

Note that it is possible to apply the guard potential Ud to the second insulator 811 instead of applying the voltage to the guide wire sheath 803. This will also reduce the potential difference across the second insulator 811 with respect to the conductor member 808. However, by applying the guard potential Ud to the guide wire sheath 803, a potential reducing effect can be utilized at the distal part of the guide wire, towards the sensor 801. Suppose a deterioration in insulating capacity occurs between any of the electrical leads 805, 806 and the guide wire sheath; a leakage of current will then occur, for example between the first lead 806 and the guide wire sheath 803. This current will be reduced in the same manner as at the insulator(s) arranged at the guide wire proximal end, by applying the guard potential Ud to the guide wire sheath 803. Hence, the concept of applying the guard potential Ud as described in this application may not only be used to reduce leakage currents at the male connector of the guide wire assembly, but along the entire length of the guide wire.

In the embodiments described in detail in connection to FIGS. 7 and 8, the guard potential Ud may be estimated, as previously discussed.

Figure 9:
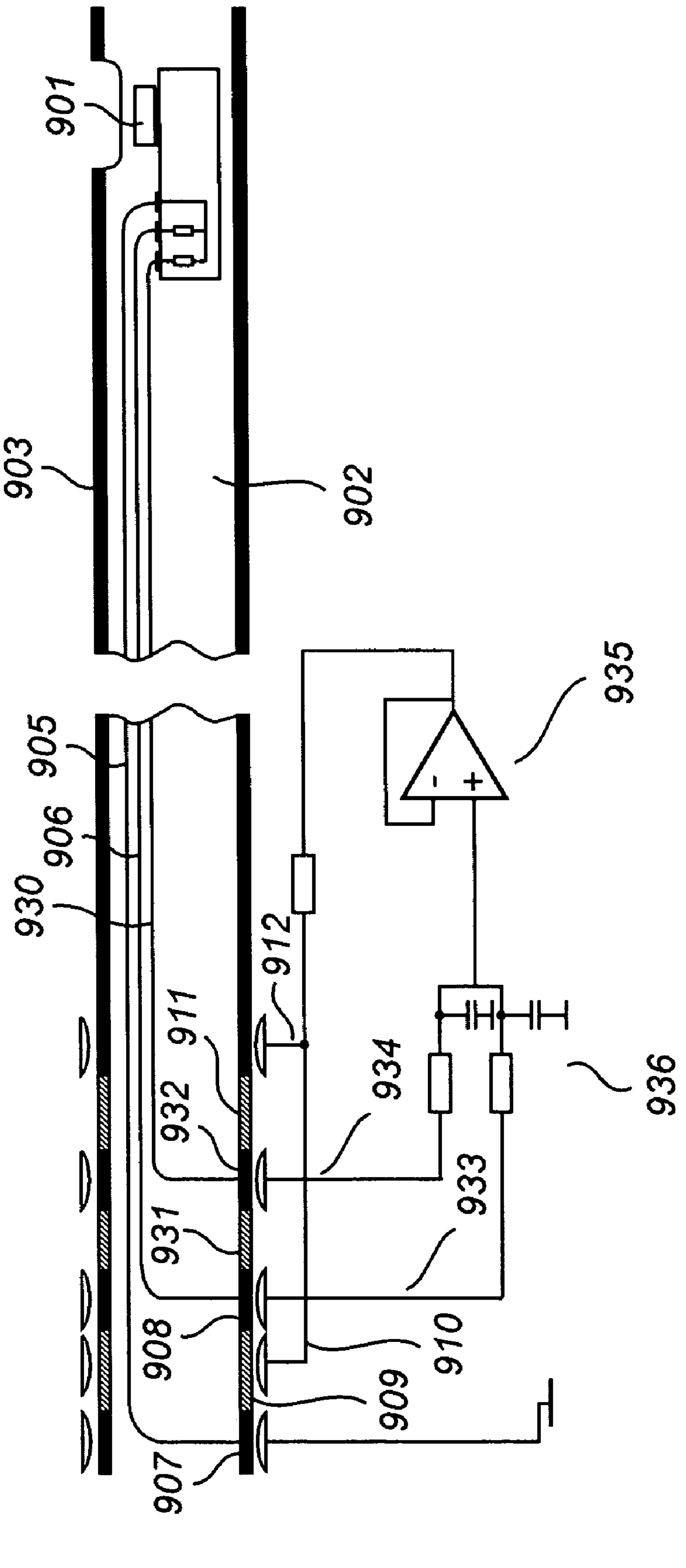
FIG. 9 shows a further embodiment of the present invention, in which two signal carrying leads and a conductive guide wire sheath are employed.

FIG. 9 shows an embodiment of the present invention, in which two signal carrying leads and a conductive guide wire sheath are employed. In this embodiment, the guard potential is set by sensing the voltage level at conducting members. A sensor 901 is mounted at a guide wire 902, and leads 905, 906, 930 are arranged to carry measurement signals from the sensor via connectors to a monitoring device (not shown). A first lead 906 carries a pressure signal, a second lead 905 is coupled to ground when in an operative state, i.e. when inserted into a female connector, and a third lead 930 carries a temperature signal. At the male connector end of the guide wire, there are three corresponding conductor members 907, 908, 932 for coupling the sensor signals carried by the first and the third leads 906, 930 to the monitoring device, and for connecting the second lead 905 to ground. In this embodiment, a conductive guide wire sheath 903 extends along the guide wire 902 and ends at a second insulator 911. Adjacent to the first conductor member 908 is a first insulator 909 separating the first conductor member 908 from the second conductor member 907. A third insulator 931 is arranged to separate the first conductor member 908 from the third conductor member 932.

Application of a guard potential Ud to the first insulator 909 by means of an electrode 910 will reduce a potential difference across the first insulator 909 with respect to the first conductor member 908 to which the signal carrying lead is connected. Hence, the corresponding leakage current will be reduced accordingly. Further, application of an additional guard potential, typically being the guard potential Ud applied to the first insulator 909, to the guide wire sheath 903 by means of an additional electrode 912 will reduce a potential difference across the second insulator 911 with respect to the third conductor member 932. Hence, the corresponding leakage current will be reduced accordingly. In this embodiment, two sensing electrodes 933, 934 are arranged to sense a voltage level of a signal at respective conductor members 908, 932 located adjacent to corresponding insulators 909, 911 across which a potential difference is to be reduced and to supply the sensed voltage to a voltage regulating circuit in the form of an operational amplifier 935.

In this particular embodiment, a low pass filter 936 is implemented at the input of the operational amplifier 935. Hence the signals of the electrodes 933, 934 are low pass filtered and added at the input of the amplifier. The output of the operational amplifier (a voltage follower configuration) is supplied as guard potential Ud via the electrodes 910, 912.

Figure 10:
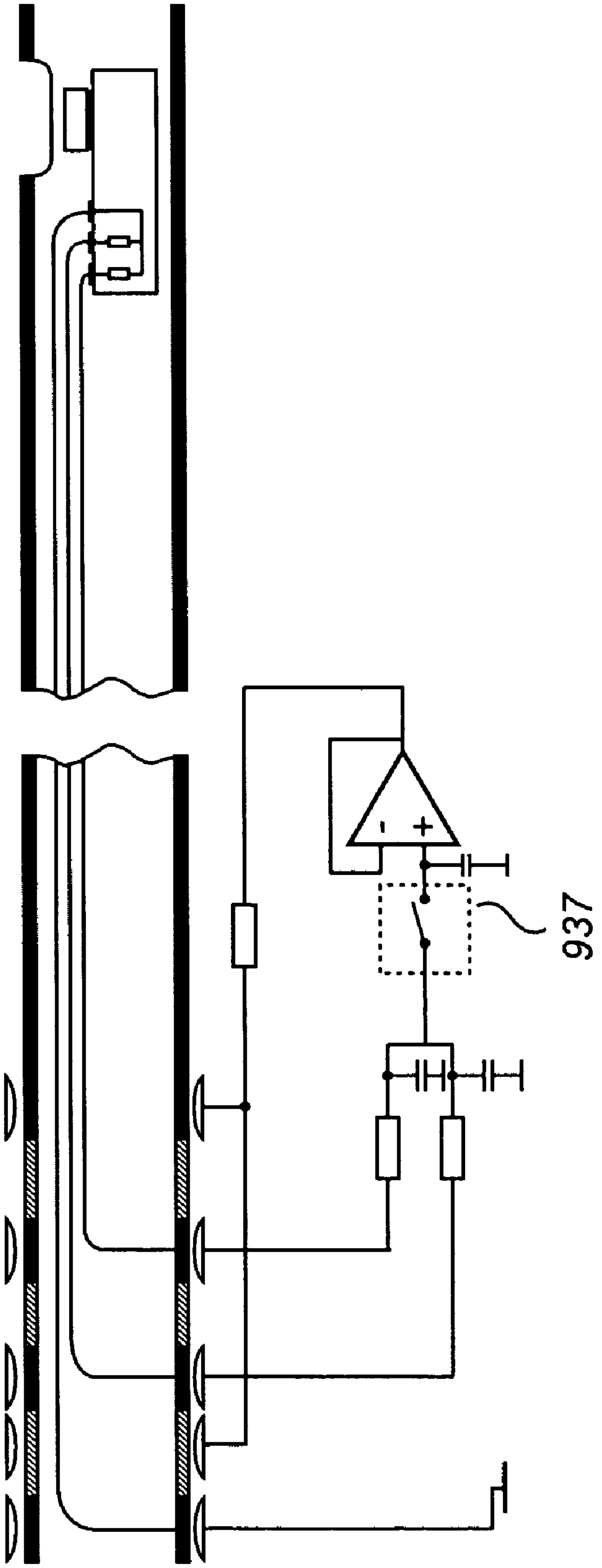
FIG. 10, shows another embodiment of the present invention, in which a sample and hold circuit is arranged at the input of a voltage follower for sampling the signal supplied to the follower.

In a further embodiment shown in FIG. 10, a sample and hold circuit 937 is arranged at the input of the voltage follower 936 for sampling the signal supplied to the follower. The guard potential Ud may be updated repeatedly by sampling the sensed signal at a particular instance of time and holding the value of the sampled signal by charging a capacitor until the next sample is taken. Alternatively, the guard potential Ud is updated once, after insertion of the male connector into the female connector, by sampling the sensed signal at one single occasion and holding the value of the sampled signal by charging the capacitor.

Figure 11:
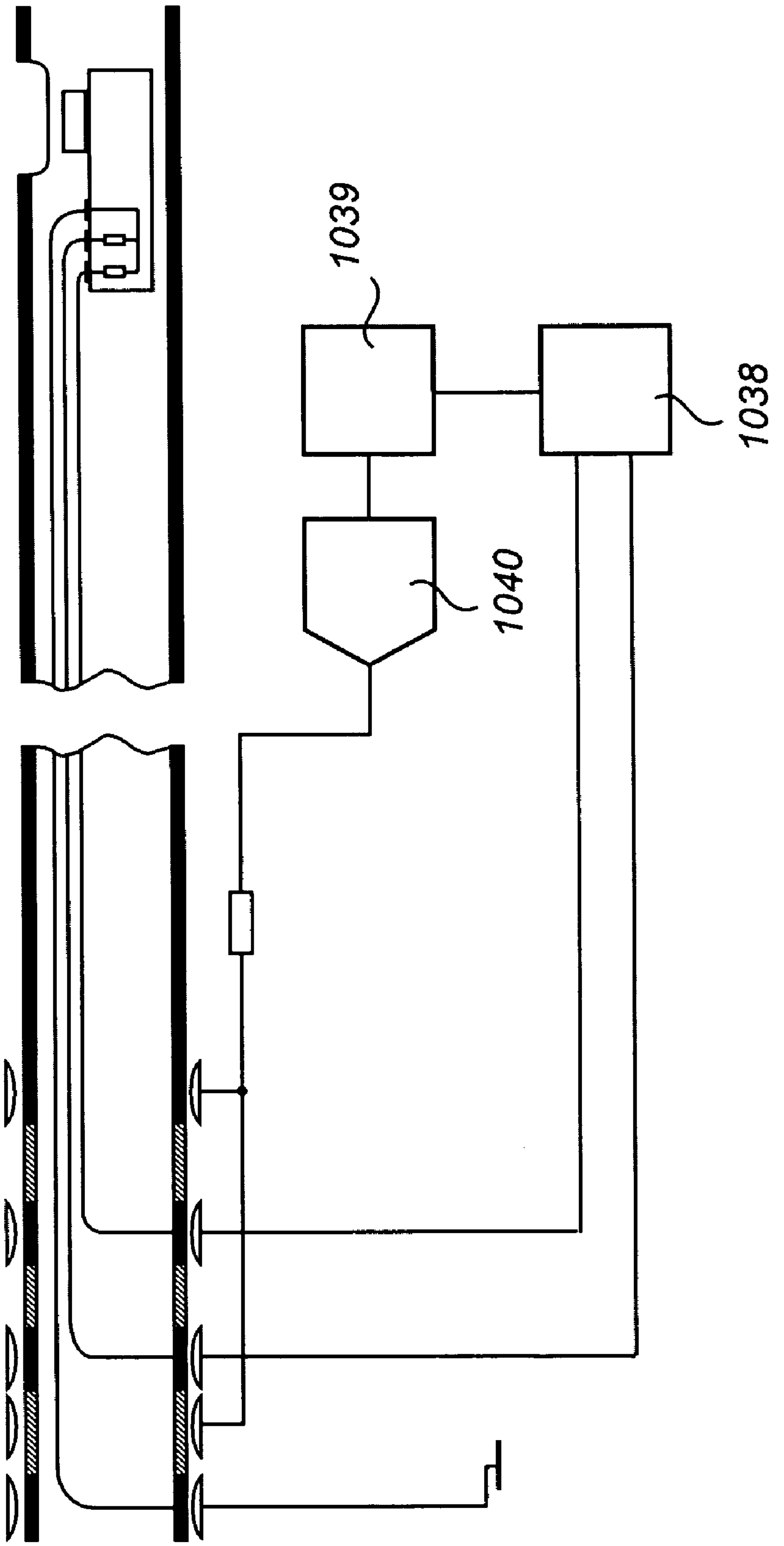
FIG. 11 shows yet another embodiment of the present invention, which utilizes an A/D converter, a microprocessor and a D/A converter.

FIG. 11 shows another embodiment, in which the low pass filter 936 and the operational amplifier 935 of FIG. 9 have been replaced by an analog-digital (A/D) converter 1038, a microprocessor 1039 and a digital-analog (D/A) converter 1040. In case a microprocessor is employed, intelligence is added to the guide wire assembly, and certain operations, such as addition of signals and averaging, may easily be implemented in the microprocessor.

Figure 12:
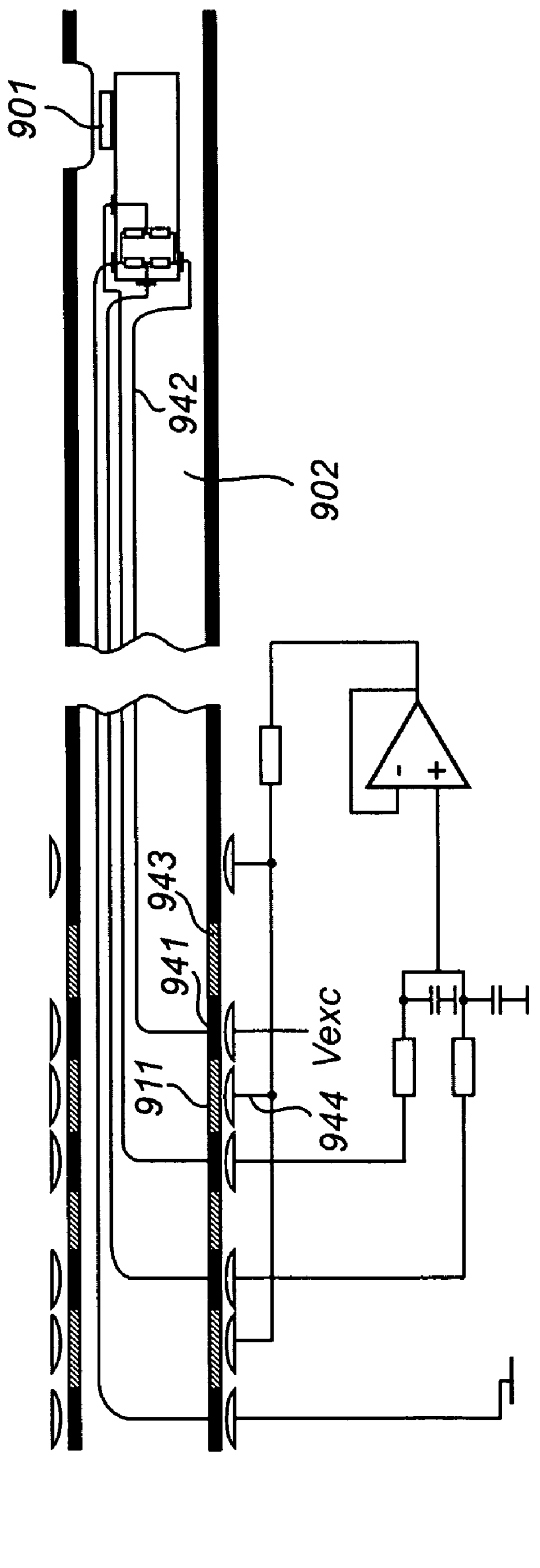
FIG. 12 shows a further embodiment of the present invention, in which two signal carrying leads, a conductive guide wire sheath and a supply voltage carrying lead are employed.

FIG. 12 shows another embodiment of the present invention, in which two signal carrying leads and a conductive guide wire sheath are employed, as in the embodiment described in connection to FIG. 9. Additionally, in this embodiment, a fourth conductor member 941 is arranged at the male connector and a corresponding fourth lead 942 is arranged in the guide wire 902. In case active sensor circuitry 901 is utilized, as is known in the art, the sensor must be provided with a supply voltage Vexc (also known as excitation voltage) in order to be operable. This supply voltage is provided to the sensor 901 from the fourth conductor member 941 via the fourth lead 942. Due to the fourth conductor member 941, a fourth insulating member 943 is arranged for separating purposes. Since the supply voltage Vexc is applied to the fourth conductor member; application of a guard potential Ud to the third insulator 911 by means of an additional electrode 944 will reduce a potential difference across the third insulator 911 with respect to the excitation voltage Vexc at the fourth conductor member 941. Hence, the corresponding leakage current will be reduced accordingly.

Even though the invention has been described with reference to specific exemplifying embodiments thereof, many different alterations, modifications and the like will become apparent for those skilled in the art. The described embodiments are therefore not intended to limit the scope of the invention, as defined by the appended claims.

The invention claimed is:

1. A method of reducing leakage current in a guide wire assembly having conductor members (707, 708) arranged at a connector end of the guide wire (702) to provide electrical contact with electrical leads (705, 706) of the guide wire and to provide signals transferred via the electrical leads to an external device, said conductor members being separated by at least one insulator (709), the method comprising the steps of:

applying, as signals are transferred via the conductor members, a separate guard potential (Ud) to said at least one insulator, which guard potential is arranged to reduce a potential difference across said insulator such that leakage current is reduced.

2. The method according to claim 1, further comprising the step of:

applying an additional guard potential (Ud) to a guide wire sheath (803), which guard potential is arranged to reduce a potential difference across an insulator (811) arranged adjacent to the guide wire sheath such that leakage current is reduced.

3. The method according to claim 1, further comprising the step of:

applying an additional guard potential (Ud) to an insulator (811) located adjacent to a guide wire sheath (803), which guard potential is arranged to reduce a potential difference across the insulator (811) arranged adjacent to the guide wire sheath such that leakage current is reduced.

4. The method according to claim 2, wherein said guard potential (Ud) and said additional guard potential (Ud) is set to be the same potential.

5. The method according to claim 1, further comprising the steps of:

estimating a voltage level of a signal at a conductor member (708) located adjacent to an insulator (709) across which potential difference is to be reduced; and supplying, as guard potential (Ud), a signal having the estimated voltage level.

6. The method according to claim 5, further comprising, in case two or more signals are transferred via respective electrical leads (906, 930) and the guide wire (902) has a conductive sheath (903), the steps of:

estimating a voltage level of a signal at a conductor member (908, 932) located adjacent to a respective insulator (909, 911) across which a potential difference is to be reduced;

creating an averaged signal having as a voltage level an average value of the estimated voltage level; and supplying, as guard potential (Ud), said averaged signal.

7. The method according to claim 1, further comprising the steps of:

sensing a voltage level of a signal at a conductor member (908, 932) located adjacent to an insulator (909, 911) across which a potential difference is to be reduced; and supplying, as guard potential (Ud), a signal having the sensed voltage level.

8. The method according to claim 7, further comprising, in case two or more signals are transferred via respective electrical leads (906, 930) and the guide wire (902) has a conductive sheath (903), the steps of:

sensing a voltage level of a signal at a conductor member located (908, 932) adjacent to a respective insulator (909, 911) across which a potential difference is to be reduced;

creating an averaged signal having as a voltage level an average value of the sensed voltage level; and supplying, as guard potential (Ud), said averaged signal.

9. The method according to claim 7, further comprising the step of:

low pass filtering the sensed voltage level such that a DC voltage level is provided as guard potential (Ud).

10. The method according to claim 9, further comprising the step of:

sampling the low pass filtered voltage and supplying the sampled voltage as guard potential (Ud).

11. The method according to claim 1, wherein the guard potential (Ud) is applied to the insulator (104) when a male connector (100) arranged at the connector end of the guide wire (102) is inserted into a female connector (200) to provide signals transferred via the electrical leads to an external device.

12. The method according to claim 1, wherein one of the conductor members (707) is connected to a reference potential.

13. A device for reducing leakage current in a guide wire assembly having conductor members (707, 708) arranged at a connector end of the guide wire (702) to provide electrical contact with electrical leads (705, 706) of the guide wire and to provide signals transferred via the electrical leads to an external device, said conductor members being separated by at least one insulator (709), the device comprising:

an electrode (710) arranged to apply, as signals are transferred via the conductor members, a separate guard potential (Ud) to said at least one insulator, which guard potential is arranged to reduce a potential difference across said insulator such that leakage current is reduced.

14. The device according to claim 13, further comprising:

a voltage regulating circuit (935, 1039) for supplying the guard potential (Ud) to the electrode (710).

15. The device according to claim 13, further comprising:

an additional electrode (812) arranged to apply an additional guard potential (Ud) to a guide wire sheath (803), which guard potential is arranged to reduce a potential difference across an insulator (811) arranged adjacent to the guide wire sheath such that leakage current is reduced.

16. The device according to claim 13, further comprising:

an additional electrode (812) arranged to apply an additional guard potential (Ud) to an insulator (811) located adjacent to a guide wire sheath (803), which guard potential is arranged to reduce a potential difference across the insulator (811) arranged adjacent to the guide wire sheath such that leakage current is reduced.

17. The device according to claim 15, further being arranged such that said guard potential (Ud) and said additional guard potential (Ud) is the same potential.

18. The device according to claim 14, further comprising:

a sensing electrode (933, 934) arranged to sense a voltage level of a signal at a conductor member (908, 932) located adjacent to an insulator (909, 911) across which a potential difference is to be reduced and to supply the sensed voltage to the voltage regulating circuit (935).

19. The device according to claim 18, further comprising, in case the guide wire assembly is arranged to transfer two or more signals via respective electrical leads (906, 930):

sensing electrodes (933, 934) arranged to sense a voltage level of a signal at a conductor member (908, 932) located adjacent to a respective insulator (909, 911) across which a potential difference is to be reduced; and a circuit (936) arranged to calculate the average value of the signals at the respective conductor members and to supply the sensed voltage to the voltage regulating circuit (935).

20. The device according to claim 18, further comprising:

a low pass filter (936) arranged to filter the sensed voltage such that a DC voltage level is provided as guard potential (Ud).

21. The device according to claim 14, wherein said voltage regulating circuit comprises an operational amplifier configuration (935).

22. The device according to claim 21, wherein the operational amplifier configuration is a voltage follower.

23. The device according to claim 21, further comprising:

a sample and hold circuit (937) arranged at the input of the operational amplifier configuration (935) for sampling the signal supplied to the operational amplifier.

24. The device according to claim 14, wherein said voltage regulating circuit comprises a microprocessor (1039).

25. The device according to claim 24, wherein a circuit arranged to calculate the average value of the signals at respective conductor members (908, 932) is implemented in the microprocessor (1039).

26. The device according to claim 24, further comprising:

an A/D-converter (1038) and a D/A-converter (1040) arranged at the microprocessor (1039).

27. The device according to claim 13, wherein one of the conductor members (707) is connected to a reference potential.

28. The device according to claim 27, wherein said reference potential to which one of the conductor members (707) is connected is a ground potential.

29. The device according to claim 13, wherein the device is arranged such that the guard potential (Ud) is applied to the insulator (104) when a male connector (100) arranged at the connector end of the guide wire (102) is inserted into a female connector (200) to provide signals transferred via the electrical leads to an external device.

30. The device according to claim 13, wherein the device is arranged at a female connector (200) of the guide wire assembly.

* * * * *